(12) United States Patent
Chen et al.

(10) Patent No.: US 10,399,927 B2
(45) Date of Patent: Sep. 3, 2019

(54) METHOD FOR PREPARING LONG-CHAIN COMPOUND

(71) Applicant: HYBIO PHARMACEUTICAL CO., LTD., Shenzhen (CN)

(72) Inventors: Youjin Chen, Shenzhen (CN); Pengcheng Mi, Shenzhen (CN); Anjin Tao, Shenzhen (CN); Jiancheng Yuan, Shenzhen (CN)

(73) Assignee: HYBIO PHARMACEUTICAL CO., LTD., Shenzhen (CN)

( * ) Notice: Subject to any disclaimer, the term of this patent is extended or adjusted under 35 U.S.C. 154(b) by 0 days.

(21) Appl. No.: 15/779,852

(22) PCT Filed: Feb. 29, 2016

(86) PCT No.: PCT/CN2016/074876
§ 371 (c)(1),
(2) Date: May 30, 2018

(87) PCT Pub. No.: WO2017/113502
PCT Pub. Date: Jul. 6, 2017

(65) Prior Publication Data
US 2018/0370904 A1 Dec. 27, 2018

(30) Foreign Application Priority Data
Dec. 31, 2015 (CN) .......................... 2015 1 1020134

(51) Int. Cl.
| | | |
|---|---|---|
| *C07C 231/02* | (2006.01) | |
| *B01J 31/00* | (2006.01) | |
| *C07C 231/14* | (2006.01) | |
| *C07C 269/06* | (2006.01) | |
| *C07C 231/12* | (2006.01) | |
| *B01J 31/02* | (2006.01) | |
| *C07C 237/22* | (2006.01) | |
| *C07B 41/12* | (2006.01) | |
| *C07B 43/06* | (2006.01) | |
| *C07C 235/08* | (2006.01) | |

(52) U.S. Cl.
CPC ......... *C07C 231/14* (2013.01); *B01J 31/0247* (2013.01); *C07C 231/02* (2013.01); *C07C 231/12* (2013.01); *C07C 237/22* (2013.01); *C07C 269/06* (2013.01); *B01J 2231/49* (2013.01); *C07B 41/12* (2013.01); *C07B 43/06* (2013.01); *C07B 2200/07* (2013.01); *C07C 235/08* (2013.01); *Y02P 20/55* (2015.11)

(58) Field of Classification Search
CPC .... C07C 231/02; C07C 231/12; C07C 269/06
See application file for complete search history.

(56) References Cited

U.S. PATENT DOCUMENTS

2010/0221749 A1 9/2010 Clave et al.
2013/0059781 A1 3/2013 Kofoed et al.

FOREIGN PATENT DOCUMENTS

| CN | 102186881 A | 9/2011 |
| CN | 103596972 A | 2/2014 |
| CN | 104395338 A | 3/2015 |
| WO | 2015055801 A1 | 4/2015 |
| WO | 2015067715 A2 | 5/2015 |

OTHER PUBLICATIONS

Sullins et al., "Total synthesis of the methanogenic cofactors methanofuran and methanofuran b," J. Am. Chem. Soc., 115(15), 6646-6651. (Year: 1993).*
Sullins David W. , et al; Total Synthes is of the Methanogen ic Cofactors Methanofuran and Methanofuran b. J. Am. Chem. Soc; Jul. 1, 1993; vol. 115, issue: 15; p. 6646-6651.
Clave Guillaume, et al; A novel heterotrifunctional peptide-based cross-linking reagent for facile access to bioconjugates. Applications to peptide fluorescent labelling and immobilization; Organic & Biomolecular Chemistry; Jun. 30, 2008; vol. 6, issue: 17; p. 3065-3078.
Peng Gao, et al; Synthesis and Gelation of N-L-glutamic Acid and N-Stearoyl-L-glutamic Diethyl Ester; Acta Chimica Sinica; Sep 30, 2004; vol. 62, issue: 9; p. 895-900.

\* cited by examiner

*Primary Examiner* — Sikarl A Witherspoon
(74) *Attorney, Agent, or Firm* — Gokalp Bayramoglu

(57) ABSTRACT

The present invention relates to a preparation method of a long-chain compound, which includes the following steps: (1) carrying out condensation reaction on H—$R_2$ and $R_5$N-Glu($OR_4$)—$OR_3$, wherein, $R_3$ is a carboxyl protecting group, $R_4$ is a carboxyl activating group, and $R_5$ is an amino protecting group; obtaining a compound of formula II; (2) removing carboxyl protecting group $R_3$ and amino protecting group $R_5$ of the compound shown in formula II to obtain a compound of formula III; (3) carrying out condensation reaction on the compound shown in formula III and

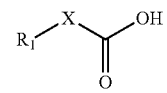

to obtain a compound shown in formula I. The method reduces the time of deprotection, and all the reactions can be carried out in a solvent with low boiling point. The post-processing requires only simple washing and recrystallization to obtain the product with higher purity, so the method is suitable for large-scale production.

20 Claims, No Drawings

METHOD FOR PREPARING LONG-CHAIN COMPOUND

CROSS REFERENCE TO RELATED APPLICATIONS

This application is the national phase entry of International Application No. PCT/CN2016/074876, filed on Feb. 29, 2016, which is based upon and claims priority to Chinese Patent Application No. CN2015110201340, filed on Dec. 31, 2015, the entire contents of which are incorporated herein by reference.

TECHNICAL FIELD

The present invention relates to the field of compound synthesis, in particular to a method for preparing a long-chain compound.

BACKGROUND

Classical peptide structures are very sensitive to proteases in vivo and degrade quickly after entering organisms. The sensitivity of the active peptide to protease can be reduced by modifying the active peptide with a long-chain compound, thereby effectively prolonging the half-life of the active peptide in the organism, and improving the possibility of using the active peptide as clinical drug.

Although there are many cases where the active peptides are successfully modified with long-chain compounds, the preparation of long-chain compound is rarely reported in the literature. A traditional preparation method uses an orthogonal protection strategy, in which protecting groups on the branched chain are removed after the synthesis of the main chain is completed. Such method will cause a reduction of solubility of the intermediate, thus a solvent with high boiling point is required in the reaction. Moreover, the post-processing is troublesome, so the method is adverse for large-scale production.

SUMMARY

In order to solve the above-mentioned problems, the present invention uses a simple synthesis method different from the conventional synthesis method, in particular, a preparation method of a compound shown in formula I is provided according to one aspect of the present invention,

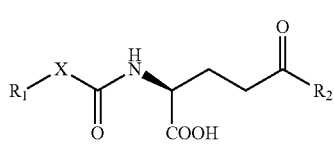

formula I wherein $R_1$ is COOH, X is $(CH_2)_m$, m is ranged from 10 to 20, preferably m is 10, 11, 12, 13, 14, 15, 16, 17 or 18, R is

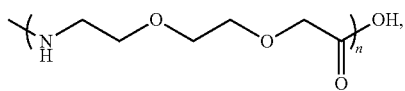

n is 1 or 2.

The synthesis method of the present invention includes the following steps:

(1) carrying out a condensation reaction on H—$R_2$ and $R_5$N-Glu(O$R_4$)—O$R_3$, wherein $R_3$ is a carboxyl protecting group, $R_4$ is a carboxyl activating group, and $R_5$ is an amino protecting group;

obtaining a compound shown in formula II

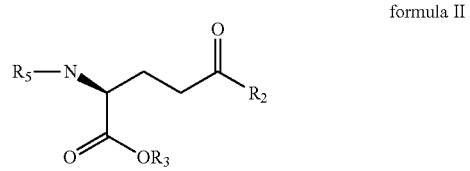

formula II (2) removing the carboxyl protecting group $R_3$ and the amino protecting group $R_5$ of the compound shown in formula II to obtain a compound shown in formula III

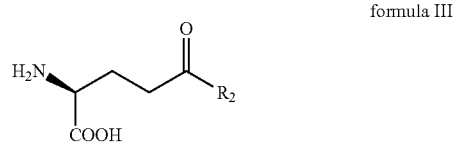

formula III (3) carrying out the condensation reaction on the compound shown in formula III and

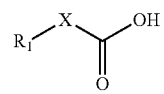

to obtain a compound shown in formula I.

Further, when n of H—R2 in step (1) equals to 2, a compound shown in formula IV is obtained by carrying out the condensation reaction on Boc-AEEA-OH and H-AEEA-OH.

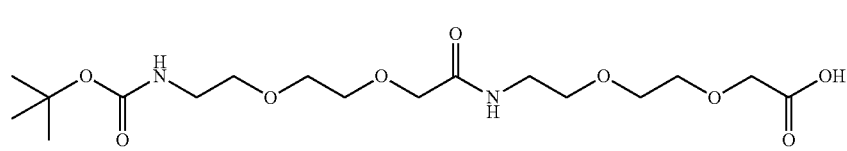

formula IV

Subsequently, a compound shown in formula V is obtained by removing an amino protecting group Boc of the compound shown in formula IV.

formula V

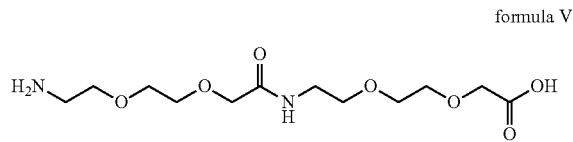 [SMILES: NCCOCCOCC(=O)NCCOCCOCC(=O)O]

Preferably, the condensation reaction of the Boc-AEEA-OH and H-AEEA-OH is carried out by activating the carboxyl group in the Boc-AEEA-OH to form an active ester and then reacting with the H-AEEA-OH.

Further, a protecting group of $R_5N$-Glu($OR_4$)—$OR_3$ in step (1) is obtained by activating a carboxyl group in the $R_5N$-Glu($OR_4$)—$OR_3$ to form an active ester.

Further, the step (3) includes first activating a carboxyl group of

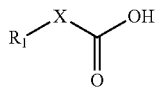

to form an active ester, and then reacting with the compound shown in formula III.

Further, the process of activating a carboxyl group and forming an active ester means to make a compound having the carboxyl group react with a condensation catalyst to form the active ester. Preferably, the condensation catalyst is selected from DCC, DIC, EDC.HCl, DAMP, HOBt, HOSu, HONb, HOAt, DCC-HOBt, DCC-HOSu, DCC-DAMP-HOBt, DCC-DAMP-HOSu, and a combination thereof. The active ester is —OBt, OSu, —ONb, or —Oat. A solvent used to form the active ester is THF or DCM. More preferably, the solvent of a reaction of the active ester Boc-AEEA-OH and the H-AEEA-OH and the solvent of a reaction of the active ester

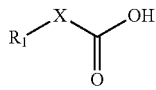

and the compound shown in formula III are water.

Further, R3 is tBu, Me or Et, $R_5$ is Boc. Preferably, $R_3$ is tBu.

Further, a reagent for removing the protecting group Boc is TFA or HCl/EA. Preferably, the reagent is TFA.

Further, a reagent for removing the amino protecting group and the carboxyl protecting group in step (2) is selected from TFA, $H_2O$, LiOH, MeOH, EtOH and a combination thereof. Preferably, the reagent is a combination of TFA and $H_2O$ (the volume ratio is 19-24:1), a combination of LiOH and MeOH, or a combination of LiOH and EtOH.

Further, step (3) is followed by a step of recrystallization, solvents used for the recrystallization are EA and EtOH, or EA and MeOH.

A compound shown as formula I obtained by the preparation method described above is provided according to another aspect of the present invention.

In the present invention, a minimum protection strategy is used in the synthesis. After a synthesis of an intermediate is completed, all protecting groups of the branched chain and the main chain are removed at the same time, and then the subsequent synthesis is proceeded. The method reduces the time of deprotection, and all the reactions can be carried out in a solvent with low boiling point. The post-processing requires only simple washing and recrystallization to obtain the product with higher purity. So the method is suitable for large-scale production.

DETAILED DESCRIPTION

Embodiment 1

Structure a

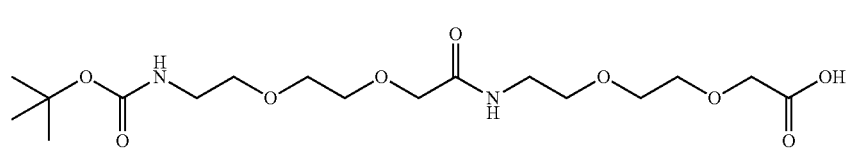

Boc-AEEA-OH (26.4 g, 100 mmol) and HOSu (12.6 g, 110 mmol) were dissolved in 200 ml tetrahydrofuran. DIC (13.9 g, 110 mmol) was added dropwise under a condition of ice bath, and the reaction was continued at room temperature for 2 h after the dropwise addition. TLC showed that the reaction of the raw materials was completed. A vacuum concentration was performed, and the residue was recrystallized with EA to obtain 33.0 g of Boc-AEEA-OSu with yield: 91%, purity: 96.7%, MS: 361.4 (M+1).

H-AEEA-OH (9.8 g, 60 mmol) and $NaHCO_3$ (8.4 g, 100 mmol) were dissolved in 100 ml deionized water, a solution of Boc-AEEA-OSu (18.0 g, 50 mmol) dissolved in THF (100 ml) was added while stirring, and after the dropwise addition was completed, the reaction was continued for 4 h. TLC showed that the reaction of Boc-AEEA-OSu had almost completed. Vacuum concentration was performed to remove the organic solvent, the aqueous phase was washed with EA (100 ml*3), the pH of the aqueous phase was adjusted to 3 with 1N HCl, and extraction was performed with EA (100 ml*2). After that, the organic phases were combined, washing was performed with saturated salt water (100 ml*3), drying was performed with anhydrous sodium sulfate, and vacuum concentration was performed to obtain 17.6 g of Boc-AEEA-AEEA-OH with yield: 86%, purity: 95.8%, MS: 409.4 (M+1).

Embodiment 2

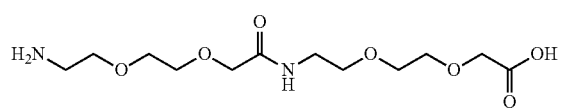

Structure b

Boc-AEEA-AEEA-OH (17.6 g, 43 mmol) was dissolved in TFA (200 ml), and stirring and reaction were performed at room temperature for 1 h. TLC showed that the reaction of the raw materials was complete. The vacuum concentration was performed to obtain 18.0 g of H-AEEA-AEEA-OH.TFA with yield: 99%, purity: 96.4%, MS: 309.3 (M+1).

Embodiment 3

Boc-Glu-OtBu (12 g, 40 mmol) and HONb (7.9 g, 44 mmol) were dissolved in THF (100 ml), a solution of DCC (8.3 g, 40 mmol) dissolved in THF (50 ml) was added while stirring, and after the dropwise addition was completed, the reaction was continued at room temperature for 2 h. TLC showed that the reaction of the raw materials had almost completed, then filtration was performed, the filtrate was subjected to vacuum concentration, and the residue was crystallized with anhydrous ether to obtain 17.2 g of Boc-Glu(ONb)-OtBu with yield: 89%, purity: 97.8%, MS: 483.6 (M+1).

H-AEEA-AEEA-OH.TFA (14.8 g, 35 mmol) and $Na_2CO_3$ (7.4 g, 70 mmol) were dissolved in 80 ml deionized water, a solution of Boc-Glu(ONb)-OtBu (17.2 g, 35 mmol) dissolved in THF (60 ml) was added while stirring, and after the dropwise addition was completed, the reaction was continued for 8 h. TLC showed that the reaction of the raw materials had almost completed. The vacuum concentration was performed to remove the organic solvent, the aqueous phase was washed with EA (100 ml*3), the pH of the aqueous phase was adjusted to 3 with 1N HCl, and extraction was performed with EA (100 ml*2). After that, the organic phases were combined, washing was performed with saturated salt water (100 ml*3), drying was performed with anhydrous sodium sulfate, and vacuum concentration was performed. The residue was crystallized with EA-n-

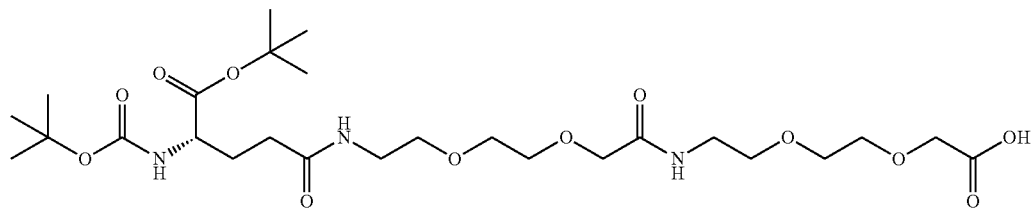

Structure c hexane to obtain 16.2 g of Boc-Glu(AEEA-AEEA)-OtBu with yield: 78%, purity: 98.7%, MS: 594.7 (M+1).

Embodiment 4

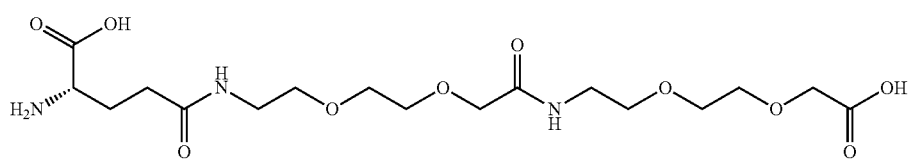

Structure d

Boc-Glu-(AEEA-AEEA)-OtBu (16.2 g, 27 mmol) was dissolved in a mixed solution of TFA (95 ml) and water (5 ml), then stirring and reaction were continued at room temperature for 2 h. TLC showed that the reaction of the raw materials was completed. Vacuum concentration was performed to obtain 14.7 g of H-Glu(AEEA-AEEA)-OH.TFA with yield: 98.6% purity: 98.9% MS: 438.4 (M+1).

Embodiment 5

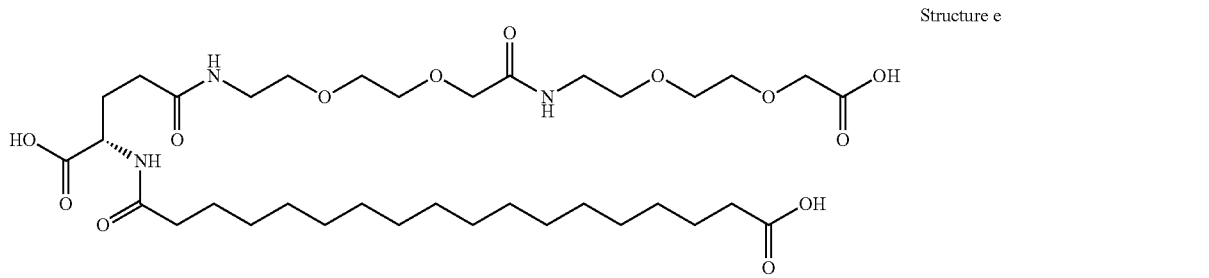 [SMILES: O=C(O)CCCCCCCCCCCCCCCCC(=O)N[C@@H](CCC(=O)NCCOCCOCC(=O)NCCOCCOCC(=O)O)C(=O)O]

Structure e

Octadecanedioic acid (1.57 g, 5 mmol), HOSu (0.58 g, 5 mmol) and DMAP (3.1 mg, 0.025 mmol) were dissolved in 50 ml of THF, a solution of DCC (1.03 g, 5 mmol) dissolved in THF (20 ml) was slowly added dropwise after stirring for 30 min, and after the dropwise addition was completed, stirring was performed overnight at room temperature. Then filtration was performed, and the filtrate was subjected to vacuum concentration. The residue was recrystallized with methanol to obtain 0.82 g of octadecanedioic acid mono-Nhydroxysuccinimide ester with yield: 40%, purity: 96.8%, MS: 412 (M+1).

H-Glu(AEEA-AEEA)-OH.TFA(1.10 g, 2 mmol) and NaHCO$_3$ (0.67 g, 8 mmol) were dissolved in a mixed solution of THF (10 ml) and water (10 ml), a solution of octadecanedioic acid mono-N-hydroxysuccinimide ester (0.82 g, 2 mmol) dissolved in THF (5 ml) was added dropwise while stirring, and after the dropwise addition was completed, stirring and reaction was continued for 4 h. Then vacuum concentration was performed to remove the organic solvent, dilution was performed with 10 ml water, washing was performed with EA (2*20 ml), pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with MeOH—H$_2$O to obtain 1.17 g of the compound shown in structure e with yield: 80%, purity: 98.7%, MS: 734.9 (M+1).

Embodiment 6

Heptadecanedioic acid (1.50 g, 5 mmol), HOSu (0.58 g, 5 mmol) and DMAP (3.1 mg, 0.025 mmol) were dissolved in 50 ml of THF, a solution of DCC (1.03 g, 5 mmol) dissolved in THF (20 ml) was slowly added dropwise after stirring for 30 min, and after the addition was completed, stirring was performed overnight at room temperature. Then filtration was performed, and the filtrate was subjected to vacuum concentration. The residue was recrystallized with methanol to obtain 0.83 g of heptadecanedioic acid mono-N-hydroxysuccinimide ester with yield: 43%, purity: 96.2%, MS: 398.5 (M+1).

H-Glu(AEEA-AEEA)-OH.TFA(1.10 g, 2 mmol) and NaHCO$_3$ (0.67 g, 8 mmol) were dissolved in a mixed solution of THF (10 ml) and water (10 ml), a solution of heptadecanedioic acid mono-N-hydroxysuccinimide ester (0.80 g, 2 mmol) dissolved in THF (5 ml) was added dropwise while stirring, and after the dropwise addition was completed, stirring and reaction were continued for 4 h. Then vacuum concentration was performed to remove the organic solvent, dilution was performed with 10 ml water, washing was performed with EA (2*20 ml), pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with MeOH—H$_2$O to obtain 1.08 g of the compound shown in structure f with yield: 75%, purity: 98.9%, MS: 720.9 (M+1).

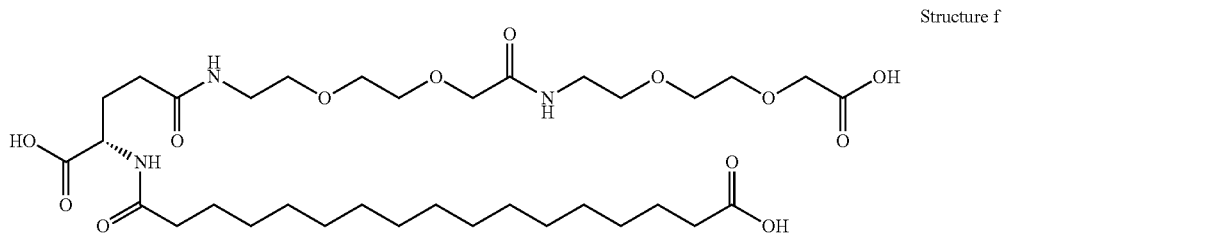 [SMILES: O=C(O)CCCCCCCCCCCCCCCC(=O)N[C@@H](CCC(=O)NCCOCCOCC(=O)NCCOCCOCC(=O)O)C(=O)O]

Structure f

Embodiment 7

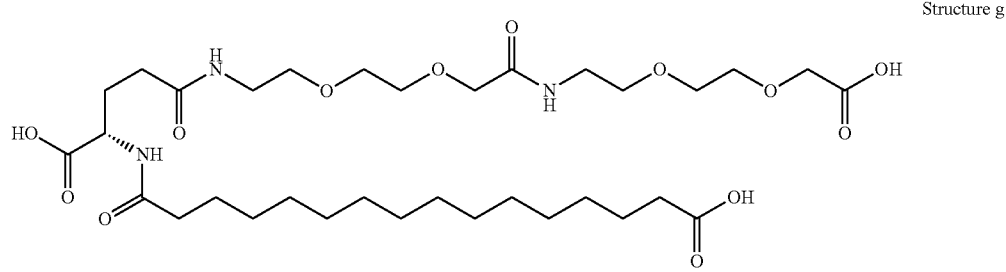 [SMILES: O=C(O)CCCCCCCCCCCCCCC(=O)N[C@@H](CCC(=O)NCCOCCOCC(=O)NCCOCCOCC(=O)O)C(=O)O]

Structure g

Hexadecanedioic acid (1.43 g, 5 mmol), HOSu (0.58 g, 5 mmol) and DMAP (3.1 mg, 0.025 mmol) were dissolved in 50 ml of THF, a solution of DCC (1.03 g, 5 mmol) dissolved in THF (20 ml) was slowly added dropwise after stirring for 30 min, and after the addition was completed, stirring was performed overnight at room temperature. Then filtration was performed, the filtrate was subjected to vacuum concentration, and the residue was recrystallized with methanol to obtain 0.79 g of hexadecanedioic acid mono-N-hydroxysuccinimide ester with yield: 41%, purity: 96.2%, MS: 384.5 (M+1).

H-Glu(AEEA-AEEA)-OH.TFA (1.10 g, 2 mmol) and NaHCO$_3$ (0.67 g, 8 mmol) were dissolved in a mixed solution of THF (10 ml) and water (10 ml), a solution of hexadecanedioic acid mono-N-hydroxysuccinimide ester (0.77 g, 2 mmol) dissolved in THF (5 ml) was added dropwise while stirring, and after the dropwise addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction performed with EA (2*20 ml). After that, the organic phases were combined, washing was performed with saturated salt water (2*20 ml), drying was performed with anhydrous sodium sulfate, and vacuum concentration was performed. The residue was crystallized with MeOH—H$_2$O to obtain 1.12 g of the compound shown in structure g with yield: 79%, purity: 98.6%, MS: 706.9 (M+1).

Embodiment 8

Nonadecandioic acid (1.43 g, 5 mmol), HOSu (0.58 g, 5 mmol) and DMAP (3.1 mg, 0.025 mmol) were dissolved in 50 ml of THF, a solution of DCC (1.03 g, 5 mmol) dissolved in THF (20 ml) was slowly added dropwise after stirring for 30 min, and after the dropwise addition was completed, stirring was performed overnight at room temperature. Then filtration was performed, the filtrate was subjected to vacuum concentration, and the residue was recrystallized with methanol to obtain 0.94 g of nonadecandioic acid mono-N-hydroxysuccinimide ester with yield: 44%, purity: 96.9%, MS: 426.6 (M+1).

H-Glu(AEEA-AEEA)-OH.TFA (1.10 g, 2 mmol) and NaHCO$_3$ (0.67 g, 8 mmol) were dissolved in a mixed solution of THF (10 ml) and water (10 ml), a solution of nonadecandioic acid mono-N-hydroxysuccinimide ester (0.85 g, 2 mmol) dissolved in THF (5 ml) was added dropwise while stirring, and after the dropwise addition was completed, the stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was carried out with EA(2*20 ml). After that, the organic phases were combined, washing was performed with saturated salt water (2*20 ml), drying was performed with anhydrous sodium sulfate, and vacuum concentration was carried out. The residue was crystallized with MeOH—H$_2$O to obtain 1.08 g of the compound shown in structure h with yield: 72%, purity: 98.5%, MS: 748.9 (M+1).

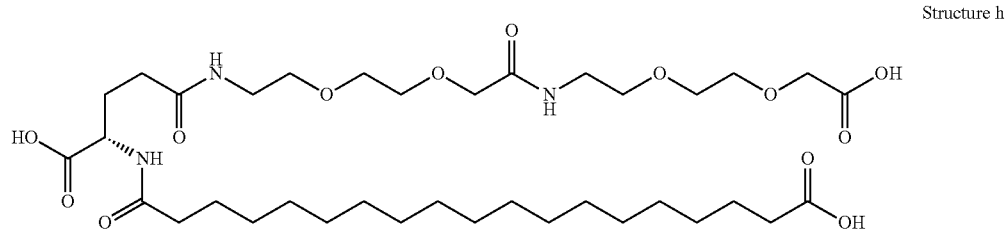 [SMILES: O=C(O)CCCCCCCCCCCCCCCCCC(=O)N[C@@H](CCC(=O)NCCOCCOCC(=O)NCCOCCOCC(=O)O)C(=O)O]

Structure h

Embodiment 9

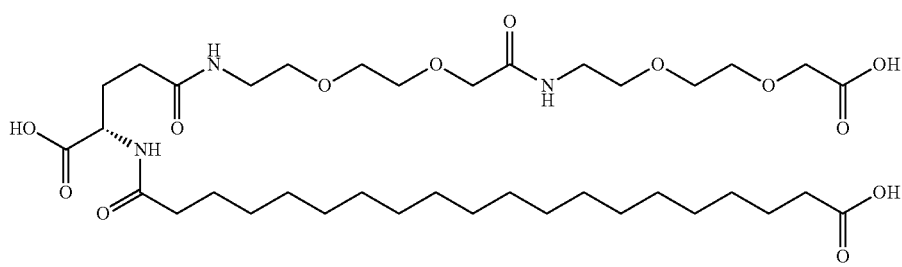
Structure i

Eicosanedioic acid (1.71 g, 5 mmol), HOSu (0.58 g, 5 mmol) and DMAP (3.1 mg, 0.025 mmol) were dissolved in 50 ml of THF, a solution of DCC (1.03 g, 5 mmol) dissolved in THF (20 ml) was slowly added dropwise after stirring for 30 min, and after the dropwise addition was completed, stirring was performed overnight at room temperature. Then filtration was performed, the filtrate was subjected to vacuum concentration, and the residue was recrystallized with methanol to obtain 0.90 g of eicosanedioic acid mono-N-hydroxysuccinimide ester with yield: 41%, purity: 95.8%, MS: 440.6 (M+1).

H-Glu(AEEA-AEEA)-OH.TFA (1.10 g, 2 mmol) and NaHCO$_3$ (0.67 g, 8 mmol) were dissolved in a mixed solution of THF (10 ml) and water (10 ml), a solution of eicosanedioic acid mono-N-hydroxysuccinimide ester (0.88 g, 2 mmol) dissolved in THF (5 ml) was added dropwise while stirring, and after the addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was carried out. The residue was crystallized with MeOH—H$_2$O to obtain 1.17 g of the compound shown in structure with yield: 77%, purity: 99.0%, MS: 762.9 (M+1).

Boc-Glu-OtBu (6.0 g, 20 mmol) and HOBt (2.97 g, 22 mmol) were dissolved in THF (50 ml), a solution of DCC (4.13 g, 20 mmol) dissolved in THF (25 ml) was added while stirring, and after the dropwise addition was completed, stirring and reaction were continued at room temperature for 4 h. TLC showed that the reaction of the raw materials had almost completed. Then filtration was performed, the filtrate was subjected to vacuum concentration, and the residue was crystallized with DCM-Et$_2$O to obtain 7.98 g of Boc-Glu(OBt)-OtBu with yield: 91%, purity: 97.6%, MS: 439.5 (M+1).

H-AEEA-OH (1.96 g, 12 mmol) and NaHCO$_3$ (1.68 g, 20 mmol) were dissolved in 100 ml deionized water, a solution of Boc-Glu(OBt)-OtBu (4.39 g, 10 mmol) dissolved in THF (20 ml) was added while stirring, and after the addition was completed, reaction was continued for 4 h. TLC showed that the reaction of the raw materials had almost completed. Then vacuum concentration was performed to remove the organic solvent, the aqueous phase was washed with EA (20 ml*3), the pH of the aqueous phase was adjusted to 3 with 1N HCl, and extraction was performed with EA (20 ml*2). After that, the organic phases were combined, washing was performed with saturated salt water (20 ml*3), and drying was performed with anhydrous sodium sulfate, and the residue was crystallized with EtOH to obtain 3.41 g of Boc-Glu(AEEA)-OtBu with yield: 87%, purity: 97.8%, MS: 393.4 (M+1).

Boc-Glu(AEEA)-OtBu (3.41 g, 8.7 mmol) was dissolved in a mixed solution of TFA (48 ml) and H$_2$O (2 ml), stirring and reaction were continued at room temperature for 2 h, then vacuum concentration was performed. The residue was washed with n-hexane for 2 times then subjected to drying to obtain 3.32 g of the compound H-Glu(AEEA)-OH.TFA shown in structure j with yield: 94%, purity: 98.2%, MS: 293.3 (M+1)

Embodiment 10

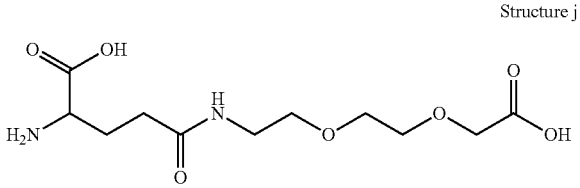 [SMILES: NC(CCC(=O)NCCOCCOCC(=O)O)C(=O)O]
Structure j

Embodiment 11

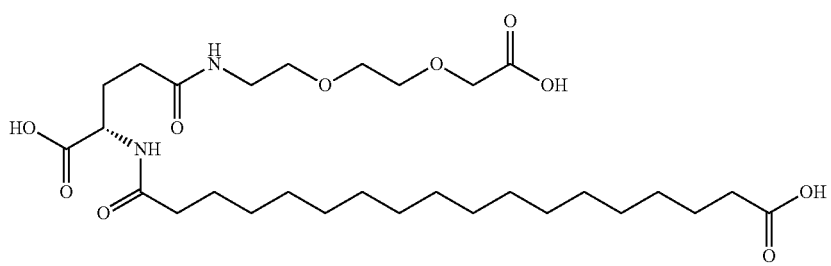
Structure k

H-Glu(AEEA)-OH.TFA (0.81 g, 2 mmol) and NaHCO₃ (0.67 g, 8 mmol) were dissolved in a mixed solution of THF (10 ml) and water (10 ml), a solution of octadecanedioic acid mono-N-hydroxysuccinimide ester (0.82 g, 2 mmol) dissolved in THF (5 ml) was added dropwise while stirring, and after the dropwise addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, vacuum concentration was performed, and the residue was crystallized with MeOH to obtain 0.91 g of the compound shown in structure k with yield: 77%, purity: 98.5%, MS: 589.7 (M+1).

Embodiment 12

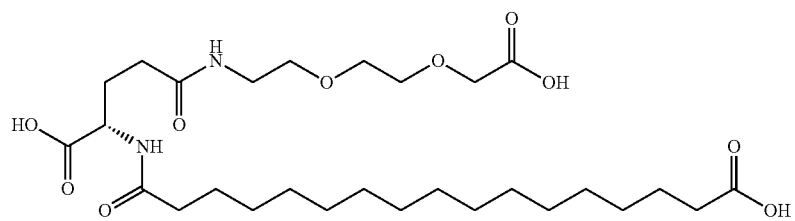

H-Glu(AEEA)-OH.TFA (0.81 g, 2 mmol) and NaHCO₃ (0.67 g, 8 mmol) were dissolved in a mixed solution of THF (10 ml) and water (10 ml), a solution of heptadecanedioic acid mono-N-hydroxysuccinimide ester (0.79 g, 2 mmol) dissolved in THF (5 ml) was added dropwise while stirring, and after the dropwise addition was completed, stirring and reaction was continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with EtOH to obtain 0.93 g of the compound shown in structure l with yield: 81%, purity: 98.9%, MS: 575.7 (M+1).

Embodiment 13

Structure m

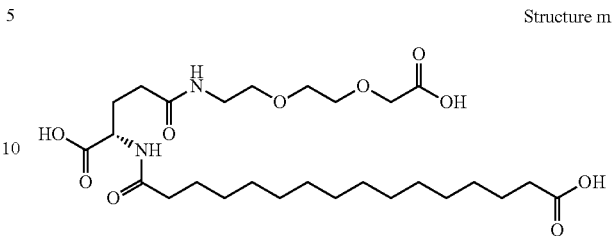

H-Glu(AEEA)-OH.TFA (0.81 g, 2 mmol) and NaHCO₃ (0.67 g, 8 mmol) were dissolved in a mixed solution of THF (10 ml) and water (10 ml), a solution of hexadecanedioic acid mono-N-hydroxysuccinimide ester (0.77 g, 2 mmol) dissolved in THF (5 ml) was added dropwise while stirring, and after the addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with EtOH to obtain 0.99 g of the compound shown in structure m with yield: 88%, purity: 98.8%, MS: 561.7(M+1).

Embodiment 14

Structure n

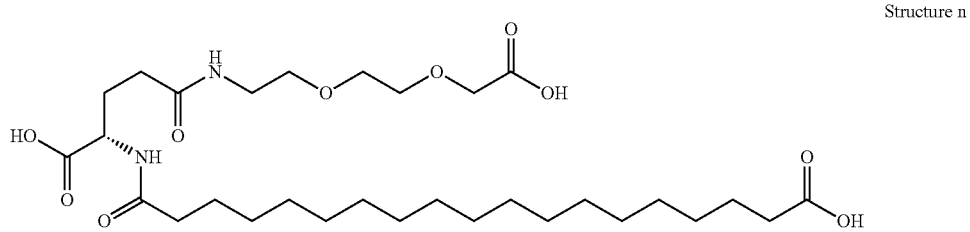 [SMILES: O=C(O)CCCCCCCCCCCCCCCCCC(=O)N[C@@H](CCC(=O)NCCOCCOCC(=O)O)C(=O)O]

H-Glu(AEEA)-OH.TFA (0.81 g, 2 mmol) and NaHCO₃ (0.67 g, 8 mmol) were dissolved in a mixed solution of THF (10 ml) and water (10 ml), a solution of nonadecandioic acid mono-N-hydroxysuccinimide ester (0.85 g, 2 mmol) dissolved in THF (5 ml) was added dropwise while stirring, and after the dropwise addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with EtOH to obtain 0.95 g of the compound shown in structure n with yield: 79%, purity: 98.6%, MS: 603.8 (M+1).

Embodiment 15

Boc-Glu-OMe (10.5 g, 40 mmol) and HONb (7.9 g, 44 mmol) were dissolved in THF (100 ml), a solution of DCC (8.3 g, 40 mmol) dissolved in THF (50 ml) was added while stirring, and after the dropwise addition was completed, the reaction was continued at room temperature for 2 h. TLC showed that the reaction of the raw materials had almost completed. Then filtration was performed, the filtrate was subjected to vacuum concentration, and the residue was crystallized with ethyl acetate to obtain 15.4 g of Boc-Glu(ONb)-OMe with yield: 91%, purity: 96.9%, MS: 423.5 (M+1).

Structure o

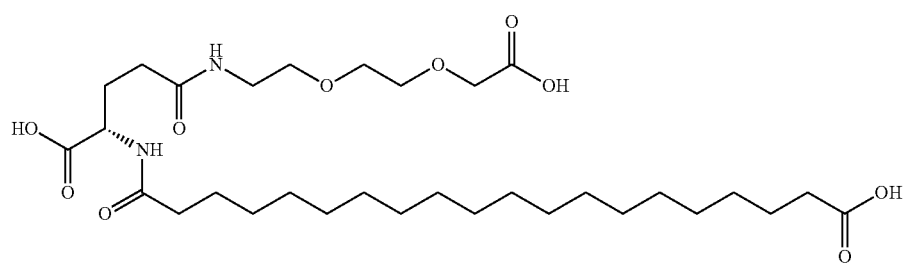

H-Glu(AEEA)-OH.TFA (0.81 g, 2 mmol) and NaHCO₃ (0.67 g, 8 mmol) were dissolved in a mixed solution of THF (10 ml) and water (10 ml), a solution of eicosanedioic acid mono-N-hydroxysuccinimide ester (0.88 g, 2 mmol) dissolved in THF (5 ml) was added dropwise while stirring, and after the addition was completed, stirring and reaction were continued for 4 h. Then vacuum concentration was performed to remove the organic solvent, dilution was performed with 10 ml water, washing was performed with EA (2*20 ml), the pH was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed. The residue was crystallized with EtOH to obtain 1.01 g of the compound shown in structure o with yield: 82%, purity: 98.9%, MS: 617.8 (M+1).

Embodiment 16

H-AEEA-AEEA-OH.TFA (14.8 g, 35 mmol) and Na₂CO₃ (7.4 g, 70 mmol) were dissolved in 80 ml deionized water, a solution of Boc-Glu(ONb)-OMe (14.8 g, 35 mmol) dissolved in THF (60 ml) was added while stirring, and after the dropwise addition was completed, the reaction was continued for 16 h. TLC showed that the reaction of the raw materials had almost completed. Then vacuum concentration was performed to remove the organic solvent, the aqueous phase was washed with EA (100 ml*3), the pH of the aqueous phase was adjusted to 3 with 1N HCl, and extraction was performed with EA (100 ml*2). After that, the organic phases were combined, washing was performed with saturated salt water (100 ml*3), drying was performed with anhydrous sodium sulfate, and vacuum concentration was performed. The residue was separated with column chromatography (MeOH:DCM=1:10) to obtain 12.5 g of Boc-Glu(AEEA-AEEA)-OMe with yield: 65%, purity: 98.5%, MS: 552.6 (M+1).

Structure p

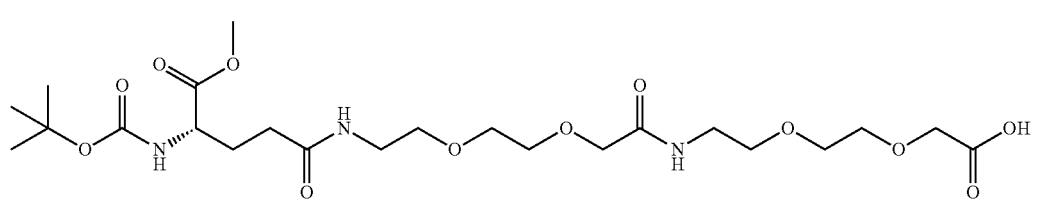

Embodiment 17

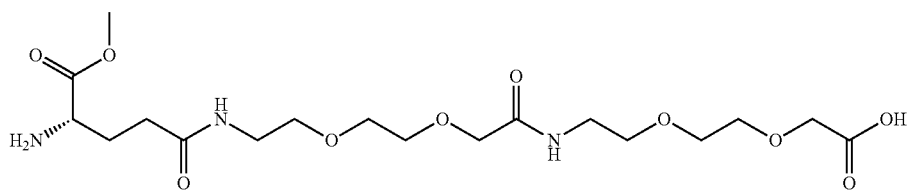

Structure q

Boc-Glu-(AEEA-AEEA)-OtM (12.5 g, 22.8 mmol) was dissolved in a mixed solution of TFA (95 ml) and water (5 ml), then stirring and reaction were continued at room temperature for 2 h. TLC showed that the reaction of the raw materials had completed. Then vacuum concentration was performed to obtain 12.4 g of H-Glu(AEEA-AEEA)-OMe.TFA with yield: 99.1% purity: 98.1% MS: 452.5 (M+1).

Embodiment 18

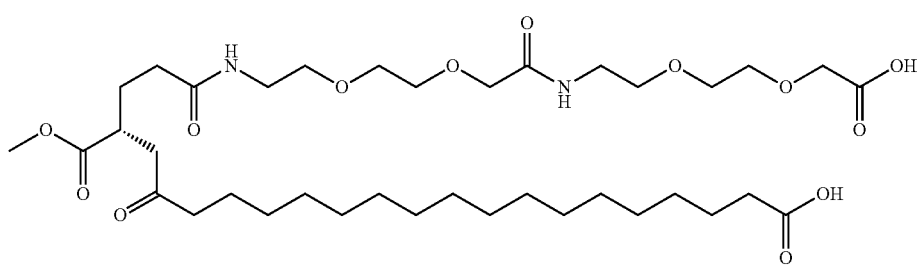

Structure r

H-Glu(AEEA-AEEA)-OMe.TFA (0.90 g, 2 mmol) and NaHCO$_3$ (0.67 g, 8 mmol) were dissolved in a mixed solution of DMF (10 ml) and water (10 ml), a solution of octadecanedioic acid mono-N hydroxysuccinimide ester (0.82 g, 2 mmol, prepared by the method according to embodiment 5 with a purity of 96.8%) dissolved in DMF (5 ml) was added dropwise while stirring, and after the dropwise addition was completed, stirring and reaction were continued for 4 h. Then vacuum concentration was performed at a temperature of 60° C. to remove the solvent. The residue was dissolved in DCM (20 ml), washed with 1N HCl (3*20 ml), then washed with saturated salt water (2*20 ml), dried with anhydrous sodium sulfate, and subjected to vacuum concentration. The residue was crystallized with MeOH—H$_2$O to obtain 1.22 g of the compound shown in structure r with yield: 82%, purity: 95.1%, MS: 747.9 (M+1).

Compound r (1.22 g, 1.64 mmol) was dissolved in a mixed solution of methanol (20 ml) and water (10 ml), then subjected to the ice bath system until the temperature was below 10° C. LiOH (0.16 g, 6.56 mmol) was added, and the ice bath reaction was continued for 4 h. Vacuum concentration was performed to remove the organic solvent, the pH of the aqueous phase was adjusted to 3 with 1N HCl, and extraction was performed with EA (2*20 ml). After that, the organic phases were combined, washing was performed with saturated salt water (2*20 ml), drying was performed with anhydrous sodium sulfate, and vacuum concentration was performed to obtain 1.06 g of the compound shown in structure e with yield: 72%, purity: 94.8%, MS: 734.9 (M+1).

What is claimed is:

1. A preparation method of a compound shown in formula I,

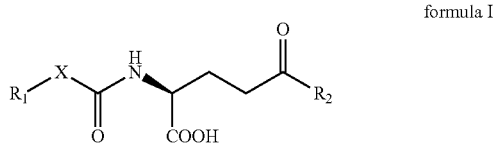

formula I wherein $R_1$ is COOH, X is $(CH_2)_m$, m is ranged from 10 to 20;

$R_2$ is

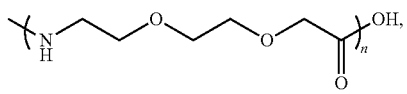

n is 1 or 2;

the preparation method comprising the following steps:

(1) carrying out a condensation reaction on H—$R_2$ and $R_5$N-Glu(OR$_4$)—OR$_3$, wherein $R_3$ is a carboxyl protecting group, $R_4$ is a carboxyl activating group selected from the group consisting of —Obt, OSu, —ONb, and —OAt, and $R_5$ is an amino protecting group, a compound shown in formula II is obtained;

formula II

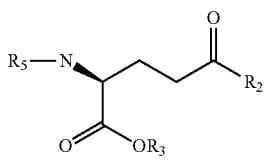

(2) removing the carboxyl protecting group R₃ and the amino protecting group R₅ of the compound shown in formula II to obtain a compound shown in formula III formula III

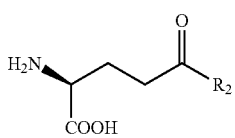

(3) carrying out a condensation reaction on the compound shown in formula III and

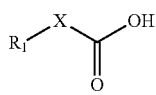

to obtain the compound shown in formula I.

2. The preparation method of the compound shown in formula I according to claim 1, wherein when n of H—R₂ in step (1) is 2, a compound shown in formula IV is obtained by carrying out a condensation reaction on Boc-AEEA-OH and H-AEEA-OH, formula IV

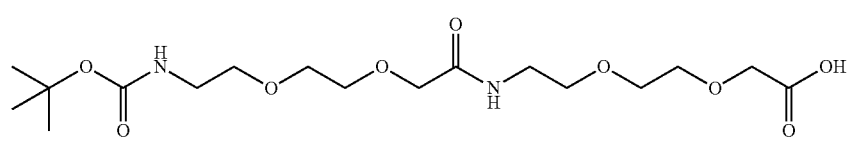

then a compound shown in formula V is obtained by removing an amino protecting group Boc of the compound shown in formula IV, formula V

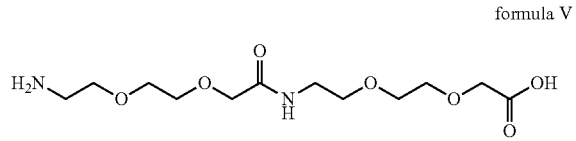 [SMILES: NCCOCCOCC(=O)NCCOCCOCC(=O)O]

the condensation reaction of Boc-AEEA-OH and H-AEEA-OH is carried out by activating a carboxyl group in Boc-AEEA-OH to form an ester and then reacting with H-AEEA-OH.

3. The preparation method of the compound shown in formula I according to claim 1, wherein a protecting group R₅N-Glu(OR₄)—OR₃ in step (1) is obtained by activating a carboxyl group in R₅N-Glu(OH)—OR₃ to form the ester.

4. The preparation method of the compound shown in formula I according to claim 1, wherein step (3) comprises activating a carboxyl group

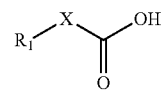

to form the ester, and reacting with the compound shown in formula III.

5. The preparation method of the compound shown in formula I according to claim 1, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

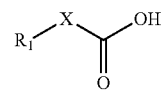

and the compound shown in formula III are water.

6. The preparation method of the compound shown in formula I according to claim 1, wherein R₃ is tBu, Me or Et, R₅ is Boc, R₃ is tBu.

7. The preparation method of the compound shown in formula I according to claim 2, wherein a reagent for removing a protecting group Boc is TFA or HCl/EA.

8. The preparation method of the compound shown in formula I according to claim 1, wherein a reagent for removing the amino protecting group and the carboxyl protecting group in step (2) is selected from the group consisting of TFA, H₂O, LiOH, MeOH, EtOH and a combination thereof, the reagent is a combination of TFA and H₂O (the volume ratio is 19-24:1), a combination of LiOH and MeOH, or a combination of LiOH and EtOH.

9. The preparation method of the compound shown in formula I according to claim 1, wherein step (3) is followed by a step of recrystallization, solvents used for the recrystallization are EA and EtOH, or EA and MeOH.

10. The preparation method of the compound shown in formula I according to claim 2, wherein a protecting group R₅N-Glu(OR₄)—OR₃ in step (1) is obtained by activating a carboxyl group in R₅N-Glu(OH)—OR₃ to form the ester.

11. The preparation method of the compound shown in formula I according to claim 2, wherein step (3) comprises activating a carboxyl group

21

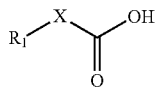

to form the ester, and reacting with the compound shown in formula III.

12. The preparation method of the compound shown in formula I according to claim 3, wherein step (3) comprises activating a carboxyl group

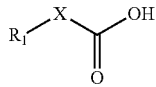

to form the ester, and reacting with the compound shown in formula III.

13. The preparation method of the compound shown in formula I according to claim 10, wherein step (3) comprises activating a carboxyl group

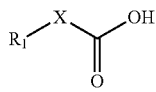

to form the ester, and reacting with the compound shown in formula III.

14. The preparation method of the compound shown in formula I according to claim 2, wherein the process of activating a carboxyl group and forming an active ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

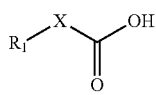

and the compound shown in formula III are water.

15. The preparation method of the compound shown in formula I according to claim 3, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

22

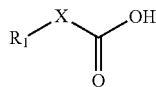

and the compound shown in formula III are water.

16. The preparation method of the compound shown in formula I according to claim 4, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

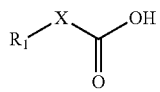

and the compound shown in formula III are water.

17. The preparation method of the compound shown in formula I according to claim 10, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

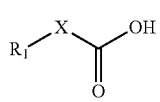

and the compound shown in formula III are water.

18. The preparation method of the compound shown in formula I according to claim 11, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

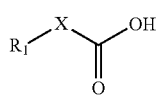

and the compound shown in formula III are water.

19. The preparation method of the compound shown in formula I according to claim 12, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the ester is one item selected from the group consisting of —OBt, OSu, —ONb, and —OAt; a solvent used to form the ester is THF or DCM, a solvent of a reaction of the ester Boc-AEEA-OH and the H-AEEA-OH and a solvent of a reaction of the ester

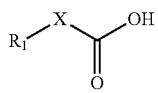

and the compound shown in formula III are water.

20. The preparation method of the compound shown in formula I according to claim 13, wherein the process of activating a carboxyl group and forming the ester comprises making a compound having the carboxyl group react with a condensation catalyst to form the ester, the condensation catalyst is selected from the group consisting of DCC, DIC, EDC.HCl, DAMP, HOBt, HOSu, HONb, HOAt, DCC-HOBt, DCC-HOSu, DCC-DAMP-HOBt, DCC-DAMP-HOSu and a combination thereof, the active ester is one item selected from the group consisting of —OBt, OSu, —ONb, and —OAt; a solvent used to form the ester is THF or DCM, a solvent of a reaction of the active ester Boc-AEEA-OH and the H-AEEA-OH and a solvent of a reaction of the ester

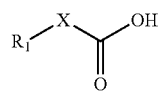

and the compound shown in formula III are water.

* * * * *